US009953818B2

(12) United States Patent
Black et al.

(10) Patent No.: US 9,953,818 B2
(45) Date of Patent: *Apr. 24, 2018

(54) SENSOR APPARATUS AND METHOD FOR USE WITH GAS IONIZATION SYSTEMS

(71) Applicant: Owlstone Medical Limited, Cambridge (GB)

(72) Inventors: Mike Black, Dhahran (SA); Matthew Hart, London (GB); John Somerville, Hertfordshire (GB); Alastair Taylor, Bury St Edmunds (GB); Iva Manasi, Cambridge (GB); Max Allsworth, Essex (GB)

(73) Assignee: Owlstone Medical Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/192,665

(22) Filed: Jun. 24, 2016

(65) Prior Publication Data
US 2017/0004958 A1    Jan. 5, 2017

Related U.S. Application Data

(63) Continuation of application No. 14/355,475, filed as application No. PCT/IB2012/002843 on Nov. 15, 2012, now Pat. No. 9,400,261.

(60) Provisional application No. 61/561,109, filed on Nov. 17, 2011.

(51) Int. Cl.
*G01N 27/62* (2006.01)
*H01J 49/04* (2006.01)
*H01J 49/40* (2006.01)
*G01N 27/68* (2006.01)

(52) U.S. Cl.
CPC ........ *H01J 49/0422* (2013.01); *G01N 27/622* (2013.01); *G01N 27/624* (2013.01); *G01N 27/68* (2013.01); *H01J 49/40* (2013.01); *H01J 49/403* (2013.01)

(58) Field of Classification Search
CPC .. G01N 27/624; G01N 27/622; H01J 49/0422
See application file for complete search history.

(56) References Cited

U.S. PATENT DOCUMENTS

| 5,420,424 | A | * | 5/1995 | Carnahan | G01N 27/624 250/281 |
| 6,774,360 | B2 | * | 8/2004 | Guevremont | G01N 27/624 250/281 |
| 8,866,075 | B2 | * | 10/2014 | Sato | G01N 27/624 250/282 |
| 9,089,279 | B2 | * | 7/2015 | Wang | A61B 5/082 |
| 9,400,261 | B2 | * | 7/2016 | Black | G01N 27/624 |
| 2004/0035183 | A1 | * | 2/2004 | O'Brien | G01N 1/2202 73/23.27 |

(Continued)

*Primary Examiner* — Wyatt Stoffa

(74) *Attorney, Agent, or Firm* — Sheppard, Mullin, Richter & Hampton LLP

(57) ABSTRACT

An ion mobility gas detector apparatus including a detector core, an inlet gas path, an exhaust gas path, a source of diluent gas, and at least one or more sensors for measuring temperature, pressure and humidity of gas streams. Further included is a mixing mechanism adapted to mix at least first and second gas streams in response to one or more sensor measurements. A controller is provided for applying drive signals to the detector core.

20 Claims, 8 Drawing Sheets

(56) References Cited

U.S. PATENT DOCUMENTS

| | | | | |
|---|---|---|---|---|
| 2004/0094704 A1* | 5/2004 | Miller | ............... | G01N 27/624 |
| | | | | 250/287 |
| 2006/0151687 A1* | 7/2006 | Miller | ............... | G01N 27/622 |
| | | | | 250/282 |
| 2007/0167853 A1* | 7/2007 | Melker | ............... | A61B 5/082 |
| | | | | 600/532 |
| 2008/0066619 A1* | 3/2008 | Petinarides | ......... | B01D 53/0454 |
| | | | | 96/4 |
| 2008/0121103 A1* | 5/2008 | Boyle | ............... | B01D 53/02 |
| | | | | 95/87 |
| 2014/0290340 A1* | 10/2014 | Murthy | ............... | G01N 1/2226 |
| | | | | 73/31.07 |
| 2016/0256072 A1* | 9/2016 | Eichler | ............... | A61B 5/097 |

\* cited by examiner

SENSOR APPARATUS AND METHOD FOR USE WITH GAS IONIZATION SYSTEMS

RELATED APPLICATIONS

This application claims the benefit of U.S. Provisional Application No. 61/561,109, filed Nov. 17, 2011 the entire contents of which is expressly incorporated herein by reference.

GOVERNMENT LICENSE RIGHTS

This application is a Continuation of U.S. patent application Ser. No. 14/355,475 filed on Apr. 30, 2014, which claims priority to PCT Publication No. PCT/IB2012/002843 filed on Nov. 15, 2012, which claims priority to U.S. Patent Application No. 61/561,109 filed on Nov. 11, 2011, all of which are incorporated herein by reference in their entirety.

FIELD OF THE INVENTION

The present invention relates to devices and methods for ion mobility systems. More specifically, the invention relates to devices and methods for detecting and compensating for certain ambient conditions ion mobility systems.

BACKGROUND OF THE INVENTION

The ability to ionize gases using ion mobility systems is useful for a wide range of applications including many chemical detection applications. Ionization techniques, in which a gas sample is ionized and then separated into constituent parts that can be detected individually, are widely used for gas composition sensing. Two well-known examples are Ion Mobility Spectrometry (IMS) and Field Asymmetric Ion Mobility Spectrometry (FAIMS), also known as Differential Mobility Spectrometry (DMS). Ion mobility detection techniques tend to be very well suited to measuring trace constituents of gas mixtures that often consist of a carrier gas with additional gases mixed in at low concentrations (for example part-per-million or part-per-billion levels). Ion mobility techniques can also be used effectively over a range of gas pressures, including pressures close to one atmosphere. This makes them useful for, amongst other things, measuring low-level impurities in air. Because they work by measuring properties of ionized molecules and because gas samples for analysis generally consist mainly of neutral molecules, ion-mobility-based detectors generally incorporate an ionizer. The sample gas is passed through the ionizer to produce a population of ionized molecules that are then manipulated in some way involving separation or selection of ionized molecules according to their behavior in an electric field, before being detected. Ionizers commonly in use include radioactive sources, light-based devices such as ultra-violet lamps, and electrostatic devices such as corona discharge ionizers.

Practical chemical detectors such as Field Asymmetric Ion Mobility Spectrometry (FAIMS) systems must compensate for varying environmental conditions as these can affect the output of the spectrometer. There are also a number of implementation challenges that the designer must overcome in order to produce a repeatable and reliable detection system. As one skilled in the art would recognize, a wide variety of non-idealities are encountered in practice. For instance, some of those most relevant to FAIMS systems fall into the following categories:

Environmental and system variations and non-uniformities (e.g. changes in temperature, pressure, humidity and pump rate);

Non-ideal device physics (e.g. charge mirroring); and

Operational constraints (e.g. must provide certain levels of efficiency and stability while maintaining performance).

In this regard, it is to be understood and appreciated changes in ambient conditions such as temperature, pressure, and ambient humidity often lead to changes in FAIMS spectra. It is noted theoretical and/or empirical corrections exist for these effects. While theoretical approaches work well for pressure and, to a lesser extent, temperature, not all environmental conditions can easily be corrected in this manner. Empirical corrections can be determined for all ambient variables, but this approach necessitates prior characterization of analytes across a multi-dimensional matrix of conditions and the storage of this data for each analyte, which can be a time consuming and laborious process. It is thus desirable to provide a system or approach that enables conditions at the sensor head to be controlled in such a system such that each analyte only has to be characterized under a small set of environmental conditions.

In regards to a FAIMS system, since it is a highly sensitive system, FAIMS spectrometers can often detect down to parts-per-billion levels or more. Direct sampling from the ambient environment can thus be problematic for such highly sensitive systems, as they can be saturated by higher concentrations of analytes or interferents, thus hiding the analytes of actual interest. High concentrations of some analytes can persist within the system as contamination due to absorption onto internal surfaces, adversely affecting performance.

It is advantageous to determine how the system behaves under known conditions. When sampling from the ambient environment there are always unknown elements of the spectra, which can make base-lining system performance troublesome.

It is noted a standalone FAIMS system typically requires a pump component to drive a flow of air through the FAIMS system. However, pumps introduce pulsatility into the flow, which can distort FAIMS spectra (for example, by altering peak positions and splitting peaks). Furthermore, the flow generated by pumps as they age, warm-up, etc. can vary, which may cause significant errors in the flow through the FAIMS system.

Further, when there is the presence of multiple species in a FAIMS system, the finite amount of charge available is typically distributed between the species according to their concentrations and charge affinities. This makes its difficult to quantitatively judge the concentration of the species present, particularly if one of these species is present in high concentrations or charge affinities.

SUMMARY OF THE INVENTION

A certain aspect of the invention relates to an Ion Mobility Spectrometry (IMS) system (such as a FAIMS) adapted and configured to detect certain conditions present within the system. In an illustrated embodiment the system includes an IMS core preferably consisting of an IMS sensor; an ionizer; a temperature sensor; and a pressure sensor. The system may further include a heated filter coupled to a temperature sensor wherein the heated filter has an inlet flow and an outlet flow coupled to the FAIMS core, which FAIMS core may include a heater element wherein an outlet flow of the FAIMS core is at least in part coupled to a scrubber. Still further, the system may include an ambient humidity and temperature sensor positioned to monitor ambient conditions in proximity to the inlet to the FAIMS core. An ambient humidity sensor is a sensor used to determine the absolute ambient humidity (normally measured in ppmv, $mg/m^3$ etc) and can be either a single or group of sensors to achieve this function. For example an absolute humidity sensor giving an output corresponding to an absolute humidity (normally measured in ppmv, $mg/m^3$ etc) or a relative humidity sensor (giving an output in % relative humidity) in combination with other sensors, primarily a temperature sensor could be used. An outlet flow of the scrubber is preferably at least in part coupled to a FAIMS sensor flow controller wherein an outlet flow of the FAIMS sensor flow controller is coupled at least in part to an outlet flow controller. In an illustrative embodiment, the system may further include a recirculating flow path coupling the outlet flow of the FAIMS sensor flow controller to the inlet flow of the FAIMS core wherein the recirculating flow path may include a scrubber, filter and a heater coupled to a temperature sensor.

Each of the outlet flow controller and FAIMS sensor flow controller may consist from the group selected from a pump run open loop; a flow sensor controlling a variable valve, a pump controlled by a flow controller and a flow restrictor with a differential pressure sensor controlling a pump.

Another aspect of the invention relates to the system being adapted and configured such that the heated inlet filter and recirculation flow filter are operated at different temperatures than the FAIMS core heater to assist heat transfer wherein the heated inlet filter and recirculation flow filter are operated at a higher temperature than the FAIMS core heater. A further aspect relates to the system being adapted and configured such that use of the FAIMS sensor flow controller and the outlet flow controller enable the dilution ratios of the system to be adjusted to increase sensitivity at low ambient analyte concentrations and decrease sensitivity at high ambient analyte concentrations.

Yet further aspects of the invention relate to the system being adapted and configured such that control of the inlet flow to the FAIMS core is controlled via control of the outlet flow controller and humidity at the FAIMS sensor is stabilized to a value at which analytes have been characterized.

Additional aspects of the invention relate to the system being adapted and configured to facilitate impact of ions onto a detector electrode so as to detect ions. Additionally, the system being adapted and configured such that an electric field is generated in the region preferably between the FAIMS filter and detector electrode to direct ions onto the detector electrode surface wherein the electric field is at least partially perpendicular to the gas flow. The system may further be adapted and configured such that carrier gas is directed through perforations provided in the detector electrode(s) and may further include features being provided in the electrode in the vicinity of the perforations to aide with capturing ions.

Yet another aspect of the invention relates to the system adapted and configured to provide only one ion polarity in the FAIMS analytical region at a time whereby a single polarity of ions can be selected upstream of the analytical region using bias electrodes to create electric fields that separate opposite polarities to prevent the undesired polarity from entering the FAIMS filter. Further, the system may be adapted and configured to operate in a low power mode to monitor for a chemical event whereby upon detection of a chemical event, the system switches to a higher discrimination mode for further analysis/identification.

BRIEF DESCRIPTION OF THE DRAWINGS

The objects and features of the invention can be understood with reference to the following detailed description of an illustrative embodiment of the present invention taken together in conjunction with the accompanying drawings in which.

WRITTEN DESCRIPTION OF CERTAIN EMBODIMENTS OF THE INVENTION

Figure 1:
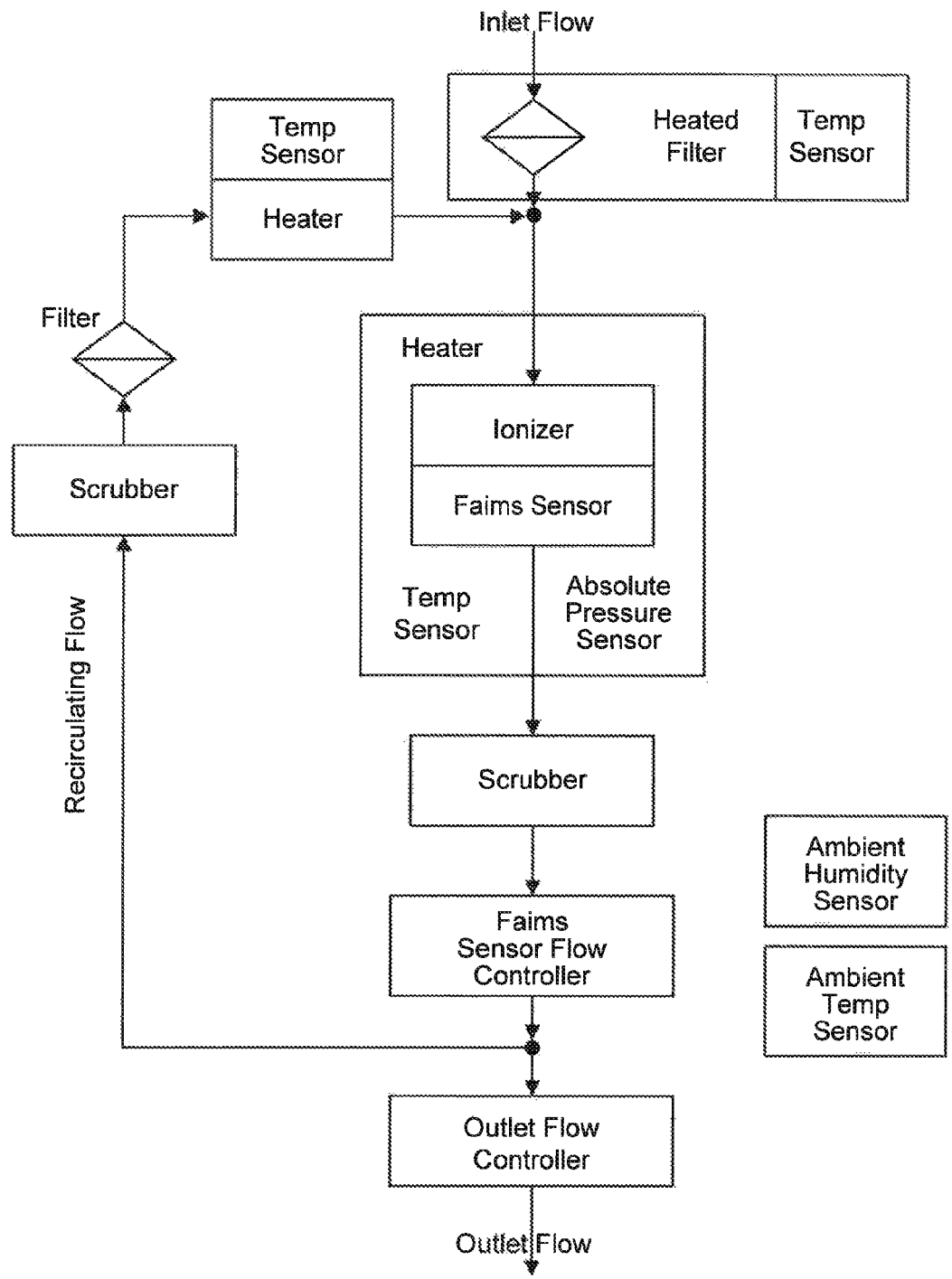
FIG. 1 illustrates a schematic of a FAIMS system in accordance with an embodiment of the invention.

The present invention is now described more fully with reference to the accompanying drawings, in which an illustrated embodiment of the present invention is shown wherein like reference numerals depict like elements. Before the present invention and specific exemplary embodiments of the invention are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials are now described. All publications mentioned herein are incorporated herein by reference to disclose and describe the methods and/or materials in connection with which the publications are cited.

It must be noted that as used herein and in the appended claims, the singular forms "a", "an," and "the" include plural referents unless the context clearly dictates otherwise. Thus, for example, reference to "a stimulus" includes a plurality of such stimuli and reference to "the signal" includes reference to one or more signals and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may differ from the actual publication dates which may need to be independently confirmed.

In regards now to the present invention, it is to be understood and appreciated changes in ambient conditions such as temperature, pressure, and ambient humidity can lead to changes in FAIMS spectra. Theoretical and/or empirical corrections exist for these effects. It is noted that while such theoretical approaches are sufficient for ambient pressure conditions and, to a lesser extent, ambient temperature conditions, not all environmental conditions can be corrected via such theoretical approaches. Empirical corrections can be determined for all ambient variables, but this approach necessitates prior characterization of analytes across a multi-dimensional matrix of conditions and the storage of this data for each analyte, which can be a time consuming and laborious process as previously mentioned. Thus, it is desirable to provide a system and/or method that enables conditions at the sensor head (e.g., in a FAIMS system) to be controlled such that each analyte only has to be characterized under a small set of environmental conditions.

As also previously mentioned, a FAIMS system is highly sensitive. For instance, FAIMS spectrometers can often detect down to parts-per-billion levels or more. Direct sampling from the ambient environment can thus be problematic for such highly sensitive systems, as they can be saturated by higher concentrations of analytes or interferents, thus hiding the analytes of actual interest. High concentrations of some analytes can persist within the system as contamination due to adsorption onto internal surfaces, adversely affecting performance.

It is thus advantageous to determine how such a system (e.g., a FAIMS system) operates under such known conditions. For instance, when sampling from the ambient environment in such systems, there are often unknown elements of the spectra, which can make base-lining system performance difficult.

As mentioned above, it is noted a standalone FAIMS system typically requires a pump component to drive a flow of air through the FAIMS system. However, pumps introduce pulsatility into the flow, which can distort FAIMS spectra (for example, by altering peak positions and splitting peaks). Furthermore, the flow generated by pumps as they age, warm-up, etc. can vary, which may cause significant errors in the flow through the FAIMS system.

And as also mentioned above, when there is the presence of multiple species in a FAIMS system, the finite amount of charge available is typically distributed between the species according to their concentrations and charge affinities. This renders it difficult to quantitatively judge the concentration of the species present, particularly if one of these species is present in high concentrations or charge affinities.

With regards now to an illustrated embodiment of the present invention, FIG. 1 depicts a FAIMS system, designated generally by reference numeral 10. System 10 is preferably defined by an air inlet flow 12 coupled to a heated filter 14 having a temperature sensor 16. The outlet flow 18 of filter 14 is coupled to a FAIMS core 20 including an ionizer 22 connected to a FAIMS SENSOR 24. An example of such an ionizer can be found in a application U.S. Application Ser. No. 61/560,592, and an example of such a FAIMS sensor 24 can be found in U.S. Application Serial Nos.: 2011/056371 and 2008/017791, all of which are hereby incorporated by reference herein in their entirety. FAIMS core 20 further preferably includes a temperature sensor 26, absolute pressure sensor 28 and heater component 30.

The outlet flow 32 of the FAIMS core 20 is coupled to a scrubber 34 which in turn is coupled to a FAIMS sensor flow controller 36. The output flow 38 of the FAIMS sensor flow controller 36 is coupled to an outlet flow controller 40 providing outlet flow 42. FAIMS System 10 preferably includes an ambient humidity sensor 44 and an ambient temperature sensor 46 positioned in a suitable location to monitor the ambient conditions at the system inlet.

FAIMS System 10 further preferably includes a recirculating flow path 45 having an input coupled to the output flow 38 of the FAIMS sensor flow controller 36, and an output coupled to the inlet flow 18 for FAIMS core 20. Recirculating flow path 45 preferably includes a scrubber 47 coupled to a filter 48, which in turn is coupled to a heater 50 having a temperature sensor 52. The significance of the aforesaid components of system 10 will become apparent from the below description of the present invention.

The FAIMS system 10 described above and shown in FIG. 1 is to be understood to be one possible configuration as other configuration will be apparent to those skilled in the art. Thus, the present invention is not to be understood to be limited to what is shown in the illustrated embodiments herein. For instance, as an illustrative example, additional flow sensing elements or filters could be added without effecting system performance.

It is to be appreciated and understood possible flow control system elements which may form the FAIMS sensor flow controller 36 and outlet flow controller 40 of FAIMS system 10 are shown in the illustrated embodiments of FIGS. 2A-2D. It is to be understood a "flow controller" is a device that can be used to control flow. It can take numerous forms and, without limitation, examples of elements that can act as a flow controller are shown in FIGS. 2A-2D. For instance, FIG. 2A illustrates a pump run open loop 210 with FIG. 2B illustrating a flow sensor 212 controlling a variable valve 214. FIG. 2C illustrates a pump 216 controlled by a flow controller and sensor 218, and FIG. 2D illustrates a flow restrictor 220 with a differential pressure sensor 222 controlling a pump 224. Controlling may for example involve using a software or hardware based feedback loop to regulate flow to a desired value(s). While it is to be understood the flow system control elements illustrated in the embodiments of FIGS. 2A-2D may be individually used in one, or both of the FAIMS sensor flow controller 36 and outlet flow controller 40 of FAIMS system 10, they are not to be understood to be limited to the only embodiments which may be used in FAIMS sensor flow controller 36 and outlet flow controller 40. Rather, any suitable embodiments meeting the objectives of the present invention may be used. For example in the steady state with a set of components connected in series mass-flow is conserved so the exact order of components is not essential to the invention. The FAIMS sensor flow controller (36) could be positioned before the scrubber (34) maintaining the functionality of the flow system. The order of the components in FIGS. 2A, 2B, 2C, and 2D could be changed both within the flow controller functional block and within the system as a whole. Additionally in FIG. 2D the flow restrictor could be any element of the system across which a pressure drop is created.

With regards to operation of FAIMS system 10 (FIG. 1), pressure correction is preferably achieved via software by scaling data into Townsends or functionally equivalent units based on the readings from the temperature sensor 26 and absolute-pressure sensor 28 at the FAIMS sensor 24. Preferably, the FAIMS scan parameters can optionally be calculated accordingly before the spectra are gathered to ensure that the appropriate compensated voltages are applied to the FAIMS sensor 24, thereby ensuring efficiency of data collection. This is preferably implemented by adjusting the FAIMS scan parameters to compensate for changes in number density, where number density is the number of molecules per unit volume. The form of the compensation is such that the ratio of electric field-to-number density is preferably kept constant. It will be obvious to someone skilled in the art that not all elements of environmental correction need applying in all circumstances.

The hardware of system 10 is temperature controlled via the heaters 14 and 50, and the temperature sensors in the inlet flow-path and recirculating flow-path 16, 52 and the FAIMS core 20 to maintain the air temperature at the FAIMS sensor 24 to a desired temperature. It is to be appreciated and understood that designing a pneumatic element to effectively transfer heat to the air is well known to those skilled in the art and in the simplest form involves assisting the diffusive heat transfer by using shorter length scales and large surface areas. However, this approach is disadvantageous for a sample inlet where increased surface area will also increase analyte hang-up and system contamination (both heat and the analyte are governed by diffusion, and while desirable for the heat to diffuse from the inlet's surfaces into the air, it is disadvantageous to have the analyte to diffuse from the air onto the surfaces). To overcome this, the present invention operates the heated inlet filter 14 and recirculation flow filter 48 at different (e.g., preferably higher) temperatures than the FAIMS sensor heater 30 to assist heat transfer. In a further alternative embodiment, the temperatures of the heated filter 14 and recirculating flow heater 48 are controlled as function of ambient temperature, inlet flow 12 and recirculating flow 45.

In accordance with the present invention, it is to be understood the recirculating flow path 45 allows clean "dry" recirculating flow ($Q_R$) to be mixed into the analyte rich and relatively wet inlet flow ($Q_I$). The ratio of recirculating flow to inlet (sample) flow is referred to as the "dilution ratio" (DR).

The geometry of system 10 is adapted and configured to permit two flow controllers (e.g., FAIMS sensor flow controller 36 and outlet flow controller 40) to be used to control the flow through the FAIMS sensor 24 ($Q_S$) and the outlet 42 ($Q_O$). Hence, it is calculated that:

$$Q_I = Q_O$$

$$DR = \frac{Q_I}{Q_R} = \frac{Q_O}{Q_S - Q_O}$$

It is to be appreciated that use of the two flow controllers (e.g., FAIMS sensor flow controller 36 and outlet flow controller 40) permits the dilution ratio to be adjusted to increase sensitivity at low ambient analyte concentrations and decrease sensitivity at high ambient analyte concentrations.

Accordingly, the system 10 of the present invention is adapted and configured to permit the control of the inlet flow 12 via the outlet flow controller 40. This is advantageous in that if flow controller 40 was placed directly in the inlet flow 12 it would be a source of contamination, chemical hang-up and reduced response speed. Further, in higher concentrations, analytes can damage or reduce the accuracy of the flow controllers. Therefore, the aforesaid flow system provided in system 10 (FIG. 1) is adapted to allow control of all flows in the system 10 whilst keeping the flow controllers (e.g., FAIMS sensor flow controller 36 and outlet flow controller 40) in clean-dry air to maximize each controller's accuracy.

Figure 2:
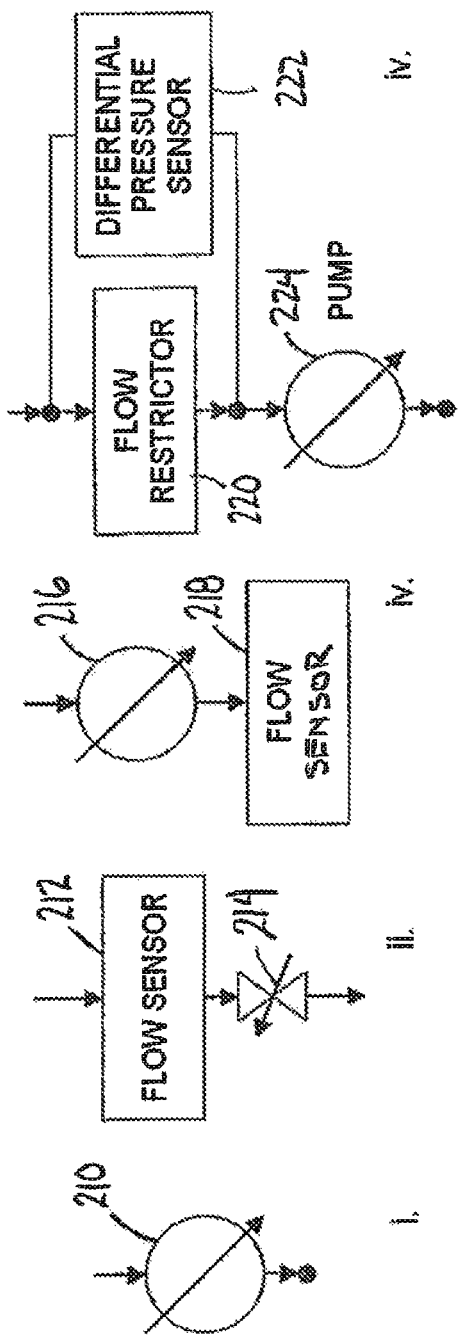
FIGS. 2A-2D illustrates respective embodiments of flow control system elements which may be embodied in the FAIMS system of FIG. 1.

It is to be understood the present invention system 10 described in reference to the illustrated embodiments of FIGS. 1 and 2 incorporate an ambient humidity sensor 44 and an ambient temperature sensor 46, adapted to accurately calculate the moisture concentration at the inlet in preferably parts-per-million by volume ($ppm_I$). Combined with the aforesaid approach for providing clean-dry air, the humidity at the sensor head 24 ($ppm_{SH}$) can be stabilized to a known reference value at which analytes have been characterized. It is to be appreciated this greatly simplifies gathering training data for the present invention system 10. Significantly, this known reference value can be achieved without monitoring the recirculating or sensor-head humidities as shown below:

$$ppm_{SH} = \frac{ppm_I Q_I + ppm_R Q_R}{Q_I + Q_R} = \frac{ppm_R DR + ppm_I}{DR + 1}$$

When $ppm_I \gg ppm_{RDR}$ $$ppm_{SH} = \frac{ppm_I}{DR + 1}$$

Therefore, calculating the humidity at the sensor head 24 from the ambient humidity sensor 44, ambient pressure sensor 28, FAIMS sensor flow controller 36 and outlet flow controller 40 allows the system 10 to operate without requiring a low ppmv level humidity sensor. This feature is especially advantageous as high accuracy low ppmv humidity sensors are both large and expensive.

Figure 3:
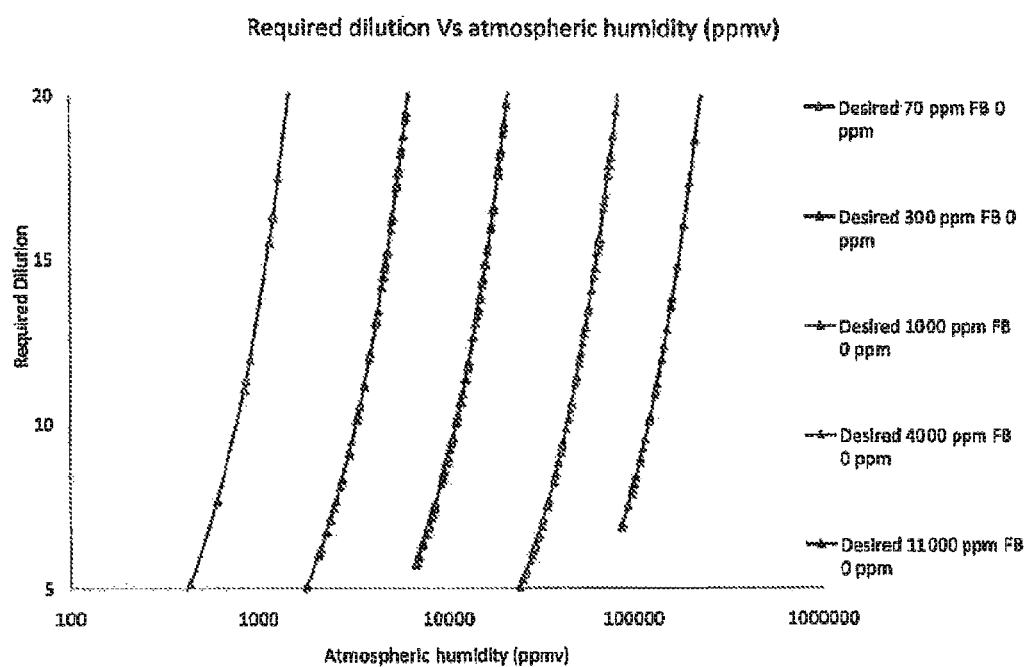
FIG. 3 illustrates a graph depicting required dilution v. atmospheric humidity.
Figure 4:
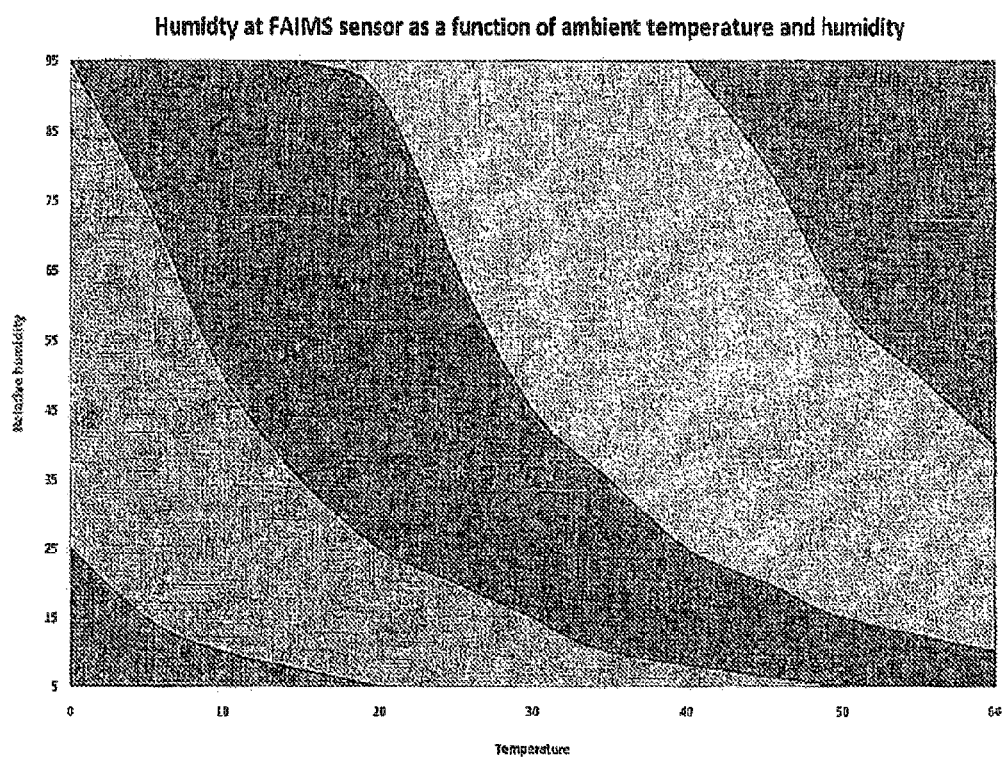
FIG. 4 illustrates a graph depicting FAIMS sensor target humidity as a function of ambient temperature and humidity.

It is further noted very large dilution ratios are undesirable because of their impact on sensitivity and are difficult to control accurately at very-high ratios. Depending upon the required operating conditions (in terms of ambient temperatures and relative humidity) it can be desirable to characterize analytes at a small range of fixed humidities. The sensor head 24 humidity can then be chosen based on the ambient temperature and humidity. Reference is now made to FIGS. 3 and 4 which illustrates the required dilution ratio with ambient humidity (ppmv) for a system working with a dilution ratio from 5 to 20 (FIG. 3) and the FAIMS sensor target humidity bands a function of ambient temperature and humidity (FIG. 4).

It is noted an alternative illustrated embodiment of the present invention is to bleed off a small portion of the inlet air and pass such air over a humidity sensor. After passing over the sensor, the air can then be recombined with the exhaust flow from the FAIMS filter. This configuration will ensure that the humidity sensor is monitoring the same air that is passing through the FAIMS filter.

As discussed herein below, it is advantageous to measure how the system 10 performs under known conditions. Using the Illustrated embodiment of the system 10 shown in FIGS. 1 and 2, the outlet flow controller 40 flow is set to zero whereby the system is operated in a recirculation mode (i.e. the full flow through the sensor head 24 is recirculation flow). In this configuration, the air in the sensor head 24 will be clean and dry allowing system performance to be measured under controlled conditions. For example, it allows the controlling software of system 10 to determine if the system 10 is contaminated, and if so, the system 10 can be left in a recirculating mode to clean-down and to allow calibration or self-test. It is noted increasing the temperature of the heaters (30, 50) will increase the speed of this process.

It is further noted the position of the reactant ion peak within the FAIMS spectra can be used to assess humidity. This is particularly true in the absence of analytes, which in some cases can affect the reactant ion peak position. In accordance with the present invention, by recirculating to remove analytes, the humidity within the system 10 can be more accurately determined. It is to be further understood the aforesaid process can also be used to determine the condition of the scrubber units (47, 34) present in the system.

And with regards to scrubbers, the illustrated embodiment of the FAIMS system 10 described with reference to FIGS. 1 and 2 requires scrubbers 34, 47 to maintain the clean-dry dilution flow. These scrubbers 34, 47 are preferably filled with particulates of carbon and molecular sieve, contain a moderate volume of air, and have a flow resistance and a plurality of paths through the scrubber. By separating the scrubber into two parts, one on either side of the pump, an effective fluidic low-pass filter is provided, screening out any pump pulsatility from the sensor head with little to no increase in system size. Adjustment may be made by changing the scrubber particle size, porosity and/or the resistance of other system elements such as filters It is noted that in the presence of multiple species present in system 10, the finite amount of charge available will be distributed between the species according to their concentrations and electron/proton affinity. This makes it difficult to quantitatively judge the concentration of the species present in system 10, particularly if one of these species is present in high concentrations or electron/proton affinity. This is typical to some degree (when an analyte is present) since the reactant ion peak will be competing with the analyte for charge to some extent.

Figure 5:
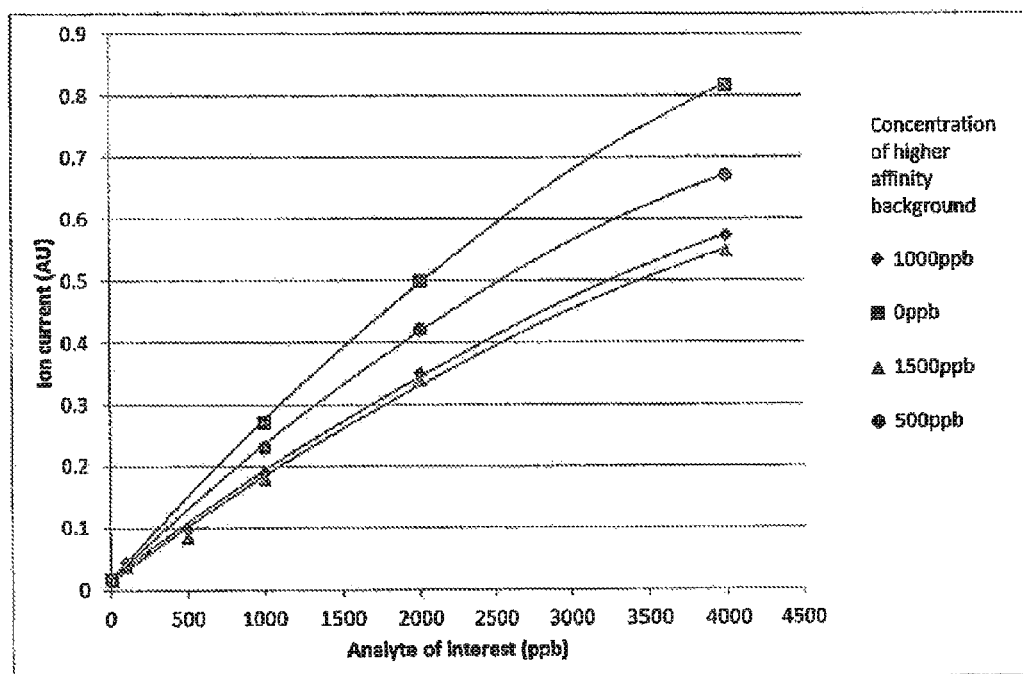
FIG. 5 illustrates a graph depicting analyte of interest v. ion current to indicate concentration of higher affinity background.

In the simplest case of a single non-dimer-forming analyte of charge affinity much greater than the reactant ions with a concentration much less than the available charge density, the height of the peak will be proportional to analyte concentration. In accordance with the present invention, when multiple analytes are present, specific analytes which are present are identified, via their FAIMS spectra. It is to be understood, if all the analyte affinities are known, then the concentrations may be scaled according to their relative affinities if the concentrations are below dimer forming levels. With reference to FIG. 5, the lower affinity analyte is suppressed non-linearly with the concentration of the higher affinity background (specifically, FIG. 5 illustrates an empirically obtained correction factor for a low affinity analyte of interest in the presence of a higher affinity background analyte wherein the matrix contains two main analytes produced from a reaction process, with concentrations verified by GC-MS for 760 individual mixtures). It is noted this relationship is predictable such that it can be compensated for. It is further noted there is also a measurable effect on the number of ions of the higher affinity analyte due to the presence of the lower affinity analyte, but this is a significantly smaller effect and, if the difference in affinity is more than 120 kJ/mol, it can often be considered inconsequential. However, if the affinities are closer, corrections need to be applied to both concentrations.

Figure 6:
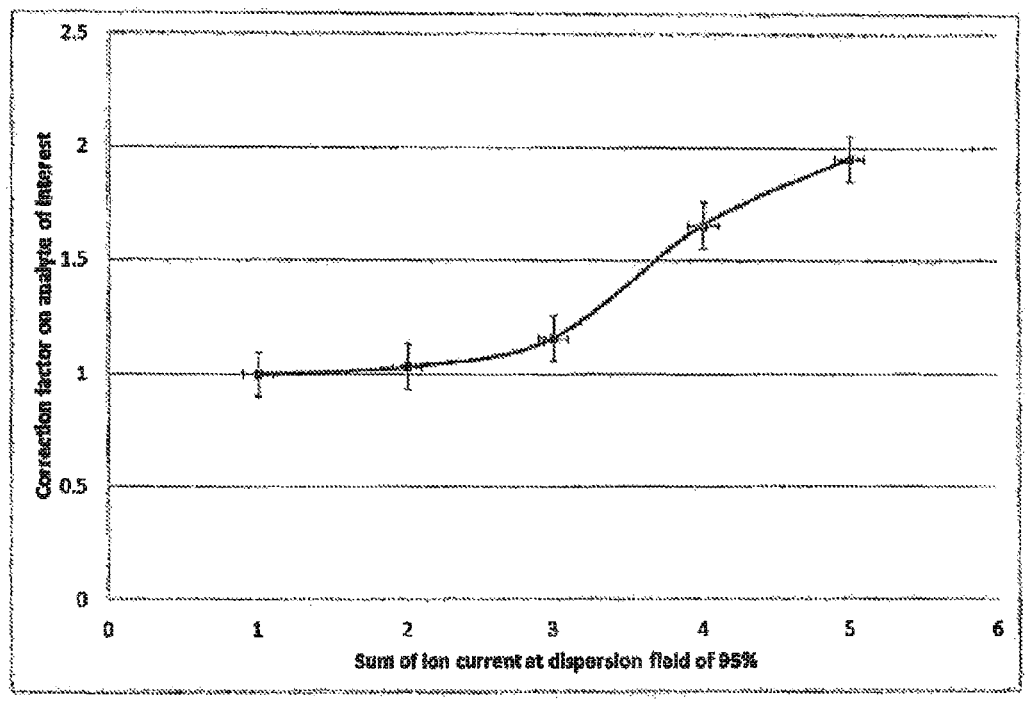
FIG. 6 illustrates a graph depicting an exemplary correction factor for an analyte.

When multiple analytes of unknown affinity are present in system 10 (for example a new unknown background interferent when looking for a known analyte), in accordance with the illustrated embodiments of the present invention, there are three ways of estimating the affinities of the unknown chemical and consequently calculate the required scaling factors, each of which is identified below:

A simple scaling of peaks with total ion current when it is above a determined threshold provides a correction factor for all peaks in a complex matrix if the RIP is still present, although it is noted this tends to overestimate concentrations but in alarm type scenarios will result in false positives rather than false negatives. FIG. 6 depicts an illustrative correction factor for an integrated ion current, and specifically an example of a correction factor for one analyte with a mixture with six other significant components and additional minor ones wherein ion current sum excludes RIP and analyte of interest.

The following relationship is used to estimate the ion affinities of the unknown analyte peaks: the change in RIP peak height versus the changes in the heights of the analyte peaks. Comparing the relative levels of change can be used to infer ion affinities and, hence, correction coefficients on for peak height (and consequently alarm levels). Alternatively, other measures of peak magnitude can be used such as the integrated current under each peak or multiple peaks.

Switching between two or more dilution ratios enables a snapshot of relative peak suppression at different concentrations. Alternatively, two channels can be run in parallel at different dilution ratios and their data compared. This can be used to determine the relative affinity of even very complex mixtures; the highest affinity chemical will have the smallest deviation from the scaled ion current when the concentration is increased. For instance, if the dilution ratio is halved, the peak that is closest to doubled (assuming not in the range of dimer formation) is the highest affinity chemical and the peak that has increased the least with the doubling of all the concentrations possesses the lowest affinity.

With regards to charge, when charge is not evenly deposited on the walls of the FAIMS filter in FAIMS system 10, a transverse electric field will be created. If this charge is not instantly dissipated then this transverse field can modify the compensation field as the ions travel through the filter, which would cause a diminished or otherwise distorted spectrum. There are two known sources of non-even distribution of charge on the FAIMS filter walls:

the DC compensation voltage: a finite scan speed leads to temporally asymmetric ion deposition on the filter sidewalls; and the RF dispersion voltage: asymmetric peak positions within a scan lead to spatially asymmetric ion deposition on the filter sidewalls Both of the above scenarios cause distortion of the FAIMS spectra in FAIMS system 10, which can include shifting, suppression, and changes in the peak width, height and other peak parameters. This is an inherent feature of FAIMS and all FAIMS systems typically exhibit these effects.

It is to be appreciated a principal cause of charge build up is insulating particles are deposited on the walls of the FAIMS analytical gap which have the potential to accumulate charge and affect the electric field in the FAIMS analytical gap.

Such particles can come from either the sampled ambient air or from the carbon and molecular sieve contents of the scrubbers. Such particulate contamination can be minimized by using suitable filtration on both the sample inlet and scrubber output flow to ensure the analytical gap is protected from particulates at all times.

It is noted the pressure drop across a filter increases rapidly with decreasing pore size and using finer filters creates an increasing burden on the system pump which can lead to larger and more power demanding systems. Additionally, as the pore size decreases the surface area of a filter increases so if very fine filters are used on the sample inlet this leads to reduced sensitivity and increased response time and hang-up.

In any FAIMS systems, but particularly in highly sensitive, small, portable or battery operated systems, removing all very fine particulates purely by filtration is typically undesirable, thus a method for coping with the charge build up associated with these particles would be advantageous to all aspects of system performance. In accordance with an illustrative embodiment of the present invention, to best remove the larger particulates (for example greater than 1 micron) without clogging filters, a two stage filtration using an initial 20 micron filter to protect a finer 1 micron filter is provided. The filters may be any type of filter such as sintered metals, open cell foams or porous polymers. Methods of operation to allow a system to be robust to small particle build up, and cancel charge buildup, are discussed below.

Figure 8:
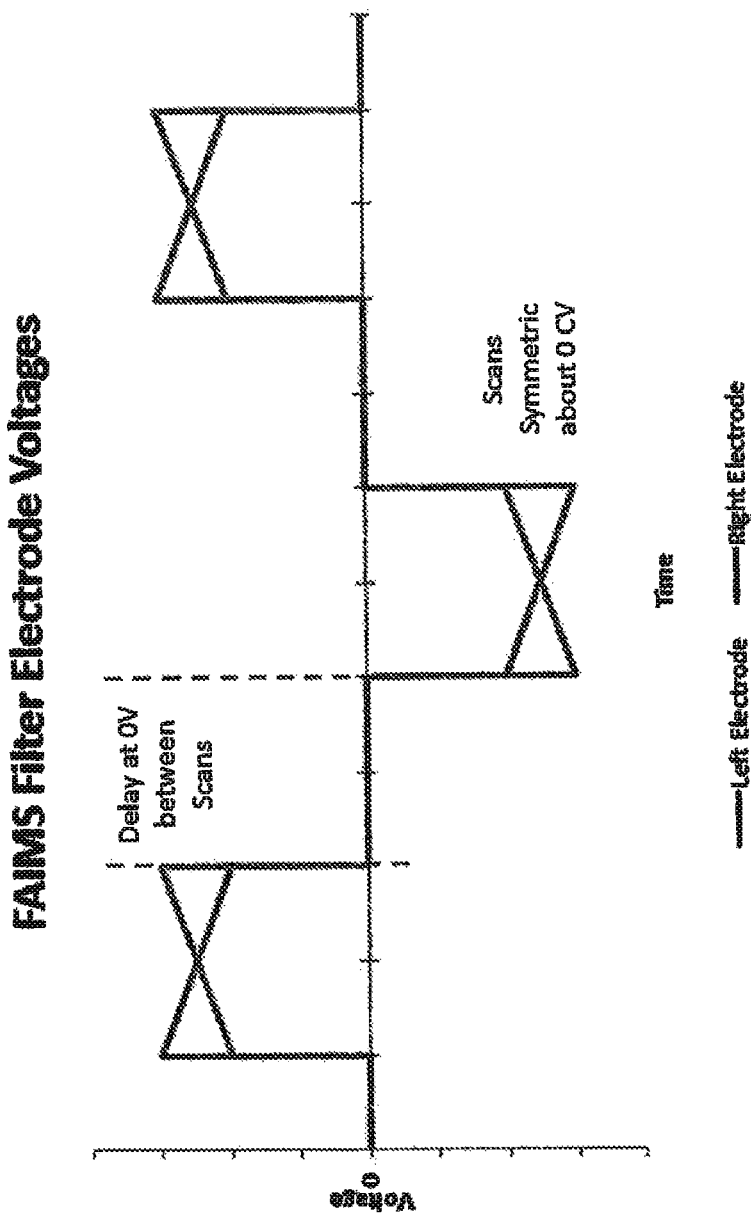
FIG. 8 illustrates a diagram using filter voltage signals to reduce charge buildup in an embodiment of the invention.

An illustrative method in accordance with the present invention includes defining the scan parameters (voltages applied to FAIMS filter and surrounding electrodes) to ensure that the time-averagedchargeaccumulation is minimized and approximately equal on both walls of the FAIMS analytical gap for example by any one of the following:

Operation at faster scan speeds (reduced charge is deposited per scan);
Flip CV scan direction, for example after each CV scan (so each scan is partially discharging any buildup form the preceding scan);
Flip CV scan direction whilst maintaining the same DF and average the result (to remove any small remaining effect);
Alternatively, flip the polarity of the CV after each CV step;
Pause with zero CV applied during or between scans (to remove any accumulated charge), for example as depicted in FIG. 8;
Or perform a CV scan at zero DF between non-zero DF scans (to remove any accumulated charge);
The system could self-recalibrate on a periodic basis to ensure that the zeroed CV is as close as possible to zero and to ensure that any CV scan is as symmetric as possible (as an asymmetric scan will lead to asymmetric charge build up);
Dynamically modify the CV scan range to improve the symmetry of ion annihilation on each side of the FAIMS channel (to maintain even build up on both surfaces of the FAIMS analytical gap); and
Operate with different static biases when collecting positive and negative ions in order to cancel out the integrated charge over time.

The following steps can be used for the aforesaid method concerning environmental conditions:
Operate at elevated temperatures, humidities, pressures and/or flow rates (to increase the electrical conductivity of the air and surfaces within the FAIMS analytical gap); and
Run at lower ion source intensities (to reduce the rate of ion deposition).

The following steps can be used for the aforesaid method concerning Radio Frequency (RF):
Pause with no RF applied during or between scans; and
Flip polarity of the RF between sequential scans in the FAIMS system.

The following steps can be used for the aforesaid method concerning components of the FAIMS system;
Use a microfabricated FAIMS filter device with a short ion residence time to provide fast scanning (e.g., an ion channel of less than 1 mm in length);
Fabricate the FAIMS filter out of an electrically conductive material such as a metal or n-type doped semiconductor or p-type doped semiconductor (to facilitate electrical discharge); and
Avoid the use of or build-up of insulating materials downstream of the ionization source until the detector (to facilitate electrical discharge).

With regards now to charge mirroring, it occurs when ions of both polarities influence the detector electrode simultaneously. This occurs when ions of the incorrect polarity impact the detector electrode (DC Mirroring) or when they capacitively couple with the detector electrode (Differential Mirroring). Charge mirroring can result in deleterious effects such as distortion of spectra in a first scenario and distortion of spectra correlating to scan speed in a second scenario.

In accordance with an illustrative embodiment of the invention, DC charge mirroring is reduced by preventing ions of the wrong polarity from impacting the detector and encouraging the correct polarity to reach the detector. This is preferably achieved by applying an electric bias: (1) between the ionization source and filter inlet; and/or (2) between the filter outlet and detector electrode(s) to direct the appropriate polarity of ions to the detector region.

It is to be understood differential charge mirroring is the charge mirroring effect characterized by an artifact in the output spectra resembling the differential of a gaussian. This is known to be due to minority ions accumulating and capacitively coupling with the detector. This effect is minimized by preventing minority ions from reaching the proximity of the ion detector. In accordance with an illustrative embodiment of the invention, minority ions can be prevented from reaching the proximity of the ion detector by preventing them from entering the filter chip. This is preferably achieved by maximizing the electric field in this region to oppose the minority ions from reaching the filter chip. The electric field can be used to either repel the minority ions until they diffuse into conductive sidewalls and are lost or to actively direct the minority ions towards a conductive surface where they can be neutralized.

It is to be appreciated that the above discussed method which removes differential mirroring, will inherently also remove DC charge mirroring. Thus, although the differential mirroring effect is usually smaller in magnitude, it is this effect that systems be configured to preferably eliminate.

In accordance with another illustrative embodiment of the invention, an alternative method for reducing the effect of differential charge mirroring is to scan a spectrum in opposite directions and to average the results. A noted shortcoming of this method is it will typically not reduce DC charge mirroring.

With regards to charge detection in a FAIMS system, it is noted successful detection of ions typically requires they impact a detector electrode. In accordance with illustrative embodiment of the invention, to encourage the impact of ions upon a detector electrode, the below discussed techniques are provided.

An electric field is generated in the region preferably between the FAIMS filter and detector electrode to direct ions onto the detector electrode surface. This field is preferably at least partially perpendicular to the gas flow. In embodiments where the carrier gas is directed through perforations provided in the detector electrode(s), ions can be lost through such perforations. Furthermore, the sizes of the perforations are selected to maximize diffusion of ions into the electrode wall while maintaining an acceptable pressure difference across the electrode. For example, the diameter of the holes is typically between 50 to 500 microns.

It is further noted that in embodiments where the carrier gas flows through perforations in the detector electrode(s), ions can flow through the perforations and go undetected. Thus, in accordance with an illustrative embodiment of the invention, an electric field is generated in the region immediately downstream of the detector electrode using, for example, a separate electrode with a fixed applied voltage, which directs any ions travelling through the detector electrode perforations back onto the detector electrode back surface, the field strength being sufficient to counteract the force that the carrier gas flow applies to the ions. Furthermore, selection of a particular electric field strength can be used to boost sensitivity to lighter gas species more than to heavier gas species. Additionally it is noted that when the reflector plate is at a fixed DC potential this will act as a virtual earth and accordingly shield the detector from Electro Magnetic Interference (EMI).

Figure 7:
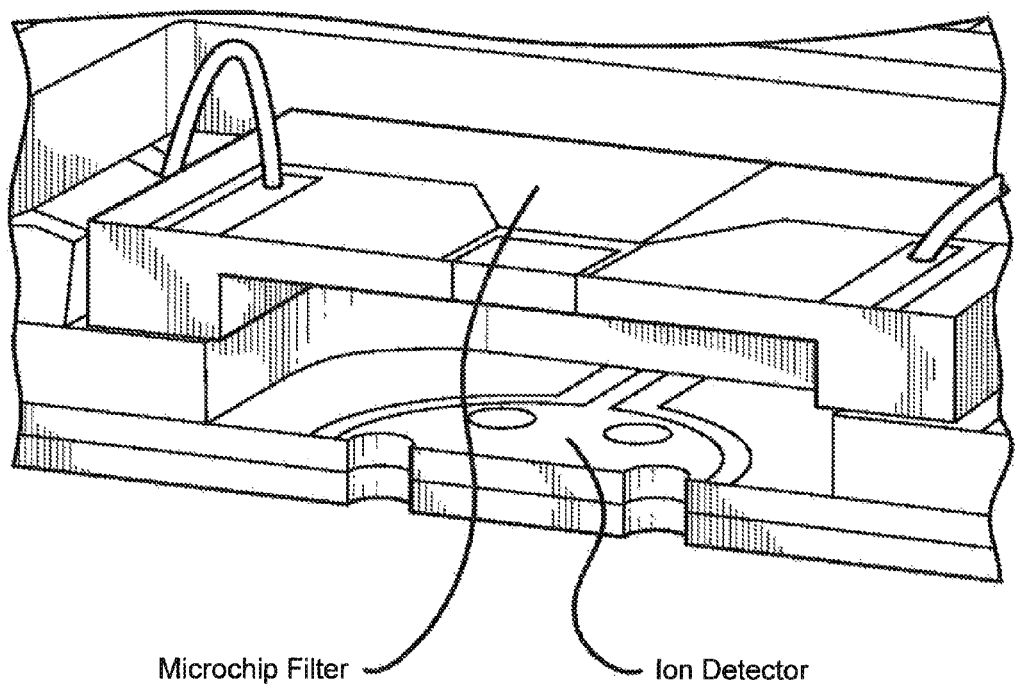
FIG. 7 illustrates a cross-sectional view of an integrated chip in accordance with an embodiment of the invention.

With regards to integration of a detector into a chip package (with reference to FIG. 7), in accordance with an illustrative embodiment of the invention, the ion detector electrode(s) are preferably integrated into the same package as the FAIMS filter. This is advantageous because the total structure would be smaller and typically less costly. Additionally, the filter structure is preferably situated in closer proximity to the detector electrode(s) allowing use of reduced voltages to maintain sufficient electric fields for efficient ion detection, providing a reduction of outgassing/contamination from ceramic chip package materials compared to PCBs providing a more leak-tight structure which can be baked at higher temperatures for clean-down.

It is further noted that in regards to upstream selection of ion polarity, and in accordance with an illustrative embodiment of the invention, it is beneficial to have preferably only one ion polarity in the FAIMS analytical region at a time, as opposite polarities will interact leading to deleterious effects such as charge cancellation and, hence, reduced sensitivity. Thus, a single polarity of ions can be selected upstream of the analytical region using bias electrodes to create electric fields that separate opposite polarities and prevent the undesired polarity from entering the FAIMS filter. The fields can also be dynamically reversed to select the opposite polarity.

With regards to certain operational constraints concerning embodiments of the aforesaid present invention, and specifically with regards to RF constraints, circuitry may preferably be included to monitor RF waveform parameters for feedback to the RF driver to maintain stable and precise performance. Waveform parameters monitored may for example include the peak voltage, peak-to-peak voltage, duty cycle, RF power consumption, and component temperatures. Furthermore, closing the loop adjusts for changes in the operating environment and component values. The feedback loop may be implemented in the analog domain, in an onboard microcontroller, externally in software, or using any combination of the above.

With regards to chemical related constraints, one method in accordance with the present invention, to achieve an energy savings, is to operate the system in a low power mode (e.g. at zero or a low value dispersion field strength) to monitor for a chemical event. On detection of a chemical event, the system can be switched to a higher discrimination mode (and hence higher power mode) for further analysis/identification. When monitoring in low power mode, the system can be triggered on, for example, certain changes in peak shape such as peak width.

The above presents a description of a best mode contemplated for carrying out the present invention, and of the manner and process of making and using them, in such full, clear, concise, and exact terms as to enable any person skilled in the art to which it pertains to make and use these devices and methods. The present invention is, however, susceptible to modifications and alternative method steps from those discussed above that are fully equivalent. Consequently, the present invention is not limited to the particular embodiments disclosed. On the contrary, the present invention encompasses all modifications and alternative constructions and methods coming within the spirit and scope of the present invention. Optional embodiments of the present invention may also be said to broadly consist in the parts, elements and features referred to or indicated herein, individually, or collectively, in any or all combinations of two or more of the parts, elements or features, and wherein specific integers are mentioned herein which have known equivalents in the art to which the invention relates, such known equivalents are deemed to be incorporated herein as if individually set forth.

The descriptions above and the accompanying drawings should be interpreted in the illustrative and not the limited sense. While the invention has been disclosed in connection with the preferred embodiment or embodiments thereof, it should be understood that there may be other embodiments which fall within the scope of the invention as defined by the following claims. Where a claim, if any, is expressed as a means or step for performing a specified function, it is intended that such claim be construed to cover the corresponding structure, material, or acts described in the specification and equivalents thereof, including both structural equivalents and equivalent structures, material-based equivalents and equivalent materials, and act-based equivalents and equivalent acts.

What is claimed is:

1. A method for mixing gas streams in an ion mobility sensor, comprising:
providing a first inlet gas stream to the ion mobility sensor;
providing a second diluent gas stream to the ion mobility sensor;
measuring at least one of temperature, pressure and humidity of each first and second gas stream; and
mixing at least the first and second gas streams in response to measurement of at least the first and second gas streams.

2. The method as recited in claim 1, wherein the ion mobility sensor further includes:

a detector core;
an inlet gas path; and
an outlet gas path.

3. The method as recited in claim 2, further including applying drive signals to the detector core.

4. The method as recited in claim 3, wherein a controller applies the drive signals to the detector core.

5. The method as recited in claim 1, wherein at least one or more sensors are used to measure the at least one of temperature, pressure and humidity of each first and second gas stream.

6. The method as recited in claim 1, wherein a mixing mechanism mixes at least the first and second gas streams in response to the measurement of at least the first and second gas streams.

7. The method as recited in claim 5, wherein the ion mobility sensor further includes a detector core, and wherein the at least one or more sensors includes a humidity sensor positioned in a gas flow path connected in parallel with the detector core whereby at least a portion of inlet gas passes over the humidity sensor.

8. The method as recited in claim 1, wherein the ion mobility sensor is a Field Asymmetric Ion Mobility Spectrometry (FAIMS) detector.

9. The method as recited in claim 8, wherein the FAIMS detector is adapted and configured to operate in a low power mode to monitor for a chemical event whereby upon detection of a chemical event, the FAIMS detector switches to a higher discrimination mode for further analysis.

10. The method as recited in claim 8, wherein the FAIMS detector includes circuitry adapted and configured to monitor RF waveform parameters for feedback to an RF driver.

11. The method as recited in claim 10, wherein the RF waveform parameters monitored include at least one of peak voltage, peak-to-peak voltage, duty cycle, RF power consumption, and component temperatures.

12. The method as recited in claim 8, wherein the FAIMS detector is adapted and configured to facilitate capture of ions of a selected polarity from a gas stream for interaction with an ion detector tier detecting ions.

13. The method as recited in claim 12, wherein the FAIMS detector is further adapted and configured to provide only one dominant ion polarity in a FAIMS analytical region at a time whereby a single polarity of ions can be selected upstream of the FAIMS analytical region using bias electrodes to create electric fields that separate opposite polarities to prevent an undesired polarity from entering a FAIMS filter.

14. The method as recited in claim 13, wherein the electric fields can be dynamically reversed to select an opposite polarity.

15. The method as recited in claim 8, wherein the FAIMS detector is adapted and configured to scan a spectrum in opposite CV directions for acquiring scan results and to combine the results.

16. The method as recited in claim 12, wherein the FAIMS detector is further adapted and configured to reduce DC charge mirroring by preventing or inhibiting ions of an incorrect polarity from impacting the ion detector and facilitating ions of a correct polarity to reach the ion detector.

17. The method as recited in claim 16, wherein an electric bias is applied between an ionization source and a FAIMS filter inlet and/or between a FAIMS filter outlet and one or more detector electrodes to direct a polarity of ions to a detector region.

18. The method as recited in claim 12, wherein the FAIMS detector is further adapted and configured to generate an electric field downstream of a detector electrode using a separate electrode having an applied voltage for driving ions traveling through detector electrode perforations back onto a back surface of the detector electrode.

19. The method as recited in claim 12, wherein an ion detector electrode is integrated in a package common with a FAIMS filter.

20. The method as recited in claim 12, wherein the FAIMS detector is further adapted and configured such that an electric field is generated in a region between a FAIMS filter and at least one detector electrode to direct ions onto a surface of the at least one detector electrode wherein the electric field is at least partially perpendicular to gas flow.

* * * * *

UNITED STATES PATENT AND TRADEMARK OFFICE
CERTIFICATE OF CORRECTION

PATENT NO. : 9,953,818 B2
APPLICATION NO. : 15/192665
DATED : April 24, 2018
INVENTOR(S) : Mike Black et al.

It is certified that error appears in the above-identified patent and that said Letters Patent is hereby corrected as shown below:

Claim 12, Column 15, Line 41:
"with an ion detector tier detecting ions." should read -- with an ion detector for detecting ions. --

Signed and Sealed this
Eleventh Day of December, 2018

Andrei Iancu
*Director of the United States Patent and Trademark Office*